(12) United States Patent
Takami

(10) Patent No.: US 6,368,270 B1
(45) Date of Patent: Apr. 9, 2002

(54) LIGHTING APPARATUS FOR ENDOSCOPE AND METHOD OF USING AN ENDOSCOPIC SYSTEM PROVIDED WITH THE LIGHTING APPARATUS

(75) Inventor: Satoshi Takami, Saitama (JP)

(73) Assignee: Asahi Kogaku Kogyo Kabushiki Kaisha, Tokyo (JP)

( * ) Notice: Subject to any disclaimer, the term of this patent is extended or adjusted under 35 U.S.C. 154(b) by 0 days.

(21) Appl. No.: 09/375,378

(22) Filed: Aug. 17, 1999

(30) Foreign Application Priority Data

Aug. 26, 1998 (JP) .......................................... 10-239764

(51) Int. Cl.[7] ................................................. A61B 1/06
(52) U.S. Cl. ....................... 600/178; 362/574; 315/129; 315/136
(58) Field of Search ................................. 600/178–181, 600/249; 362/572, 574; 315/129, 136

(56) References Cited

U.S. PATENT DOCUMENTS 3,641,332 A  *  2/1972  Reick et al. ................ 362/572
5,196,884 A  *  3/1993  Sugiyama et al. .......... 355/200
5,274,611 A  * 12/1993  Donohoe ..................... 368/10
5,830,121 A    11/1998  Enomoto et al.

FOREIGN PATENT DOCUMENTS

| JP | 1-77612 | 5/1989 |
| JP | 4-324412 | 11/1992 |
| JP | 8-321019 | 12/1996 |

* cited by examiner

Primary Examiner—John Mulcahy
(74) Attorney, Agent, or Firm—Greenblum & Bernstein, P.L.C.

(57) ABSTRACT

A lighting apparatus for an endoscope, includes: a light source for emitting light which is transmitted to a distal end of the endoscope via a light guide of the endoscope; a consumption recording device for recording the consumed light-emission time of the light source; and an indicating device for indicating information on the remaining life of the light source in accordance with data recorded in the consumption recording device; wherein the light source, the consumption recording device and the indicating device are provided in one unit.

12 Claims, 4 Drawing Sheets

LIGHTING APPARATUS FOR ENDOSCOPE AND METHOD OF USING AN ENDOSCOPIC SYSTEM PROVIDED WITH THE LIGHTING APPARATUS

BACKGROUND OF THE INVENTION

1. Field of the Invention

The present invention relates to a lighting apparatus used for an endoscope that is provided with an electric bulb which supplies illumination light to the endoscope, and also relates to a method of using an endoscopic system provided with the lighting apparatus.

2. Description of the Related Art

FIG. 4 shows a conventional endoscopic system provided with an endoscope 1, a video processor 2, a TV monitor 3 and a lighting apparatus 4. The lighting apparatus 4 is provided with an electric bulb 5 (shown by a dotted line).

The endoscope 1 is provided therein with a light guide (not shown) for leading the light emitted from the bulb 5 to an insertion tip (distal end) 1a of the endoscope 1, and an image guide (not shown) for transmitting the light reflected by a subject to be examined (e.g., inner portion of a living body) to the video processor 2. The light guide is connected with the bulb 5 via a connector 7, while the image guide is connected with the video processor 2 via the connector 7. The video processor 2 is provided therein with an image pick-up device (not shown) and performs an image processing operation in which the aforementioned reflected light is converted into electrical image signals by the image pick-up device. The electrical image signals are output to the TV monitor to be displayed thereon as an image of the subject which is to be examined.

The video processor 2 is provided therein with a time counter 6 for cumulatively counting the time (ON time) of light emission of the bulb 5 to inform the user of the total consumed lighting-time of the bulb 5. Taking account of the total consumed lighting-time of the bulb 5, the user of the endoscopic system can replace the bulb 5 before the total consumed lighting-time exceeds the life span of the bulb 5. This prevents the amount of light emitted by the bulb 5 from decreasing due to usage over a long-term, and also prevents the bulb 5 from burning out during the use of the endoscopic system.

In such a conventional endoscopic system, since the endoscope 1, the video processor 2 and the lighting apparatus 4 are connected to one another via the connector 7, the video processor 2 and the lighting apparatus 4 may not necessarily be used as a pair at all times. In other words, the video processor 2 may be disconnected from the connector 7 to be replaced with a new video processor while the lighting apparatus 4 remains in use, or vice versa. Therefore, there is a probability of the total consumed lighting-time of the video processor 2 not corresponding to the total consumed lighting-time of the bulb 5. Accordingly, it is difficult to precisely determine the time for the replacement of the bulb 5.

SUMMARY OF THE INVENTION

An object of the present invention is to provide a lighting apparatus used for an endoscope that is provided with an electric bulb, wherein the time for replacing the bulb with a new one can be reliably and precisely determined to prevent the amount of light emitted by the bulb from decreasing due to usage over a long-term, and also to prevent the bulb from burning out during the use of the endoscope system.

Another object of the present invention is to provide a method of using an endoscope system provided with such a lighting apparatus.

To achieve the object mentioned above, according to an aspect of the present invention, there is provided a lighting apparatus for an endoscope, including: a light source for emitting light which is transmitted to a distal end of the endoscope via a light guide of the endoscope; a consumption recording device for recording the consumed light-emission time of the light source; and an indicating device for indicating information on the remaining life of the light source in accordance with data recorded in the consumption recording device; wherein the light source, the consumption recording device and the indicating device are provided in one unit.

Preferably, the consumption recording device operates when a recording voltage is applied to the light source to emit light therefrom.

Preferably, the recording voltage is obtained by reducing the voltage of power supplied to the light source.

Preferably, light source is replaceable.

Preferably, a reset switch is also included for initializing the consumption recording device to reset the recorded data.

Preferably, the reset switch initializes the consumption recording device when the light emitter is disconnected from or connected to the lighting apparatus.

Preferably, the light source is an electric bulb.

Preferably, a casing is also included which accommodates the light source, the consumption recording device and the indicating device; wherein the indicating device includes an LCD fixed to the casing.

According to another aspect of the present invention, there is provided a method of using an endoscope system having an endoscope and the lighting apparatus, wherein the method includes a step of: replacing light source with a new light source when the indicating device indicates information informing that the value of the total time of light emission of the light source has reached a predetermined value.

According to another aspect of the present invention, there is provided a lighting unit including: a replaceable electric bulb for emitting light which is transmitted to a distal end of an endoscope via a light guide of the endoscope; a recorder which accumulatively stores the consumed lighting time of the electric bulb; and an indicator for indicating information on the remaining life of the electric bulb in accordance with data recorded in the recorder.

The present disclosure relates to subject matter contained in Japanese Patent Application No.10-239764 (filed on Aug. 26, 1998) which is expressly incorporated herein by reference in its entirety.

BRIEF DESCRIPTION OF THE DRAWINGS

The present invention will be described below in detail with reference to the accompanying drawings in which.

DESCRIPTION OF THE PREFERRED EMBODIMENT

Figure 1:
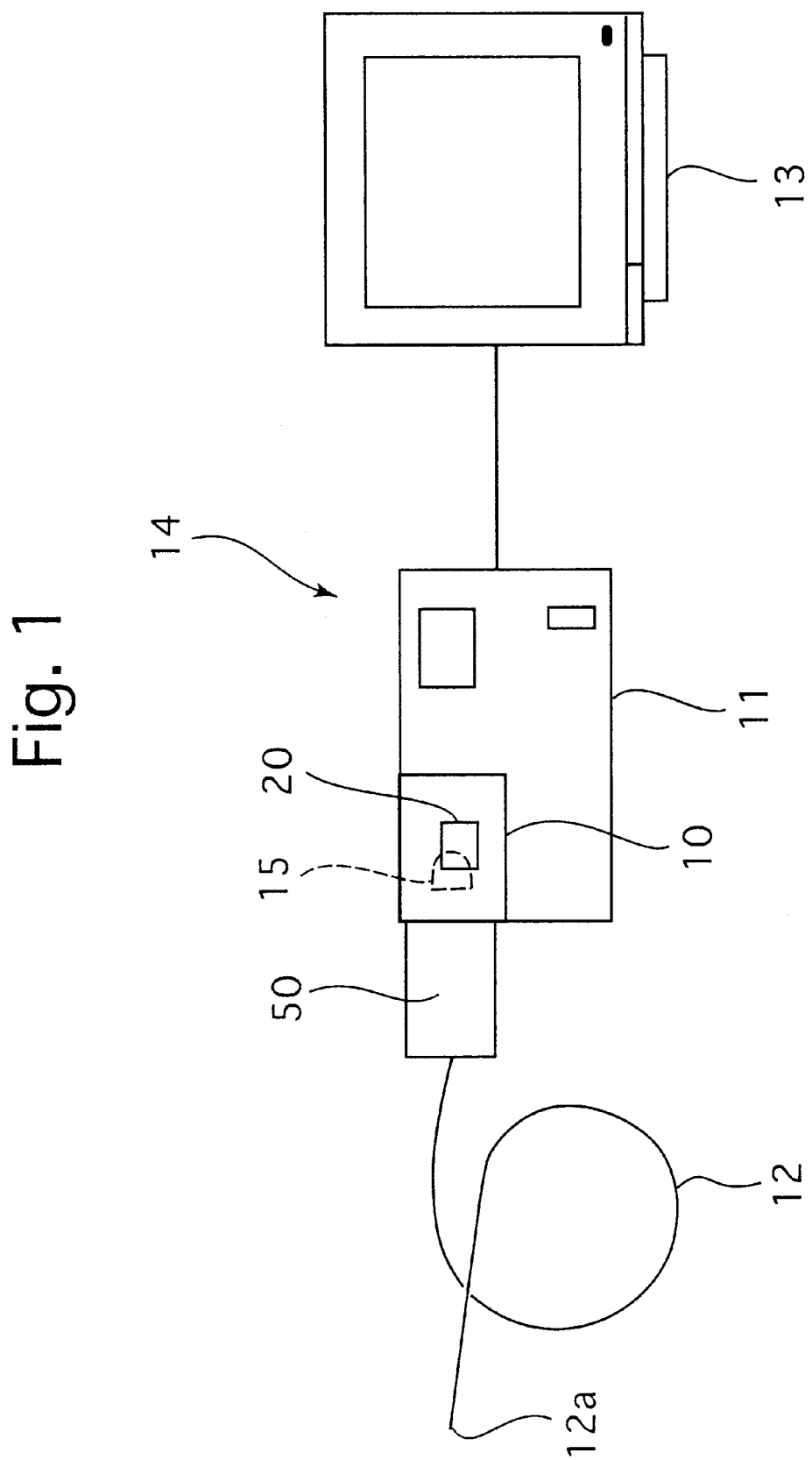
FIG. 1 is a schematic illustration showing an endoscope system having a lighting apparatus for an endoscope to which the present invention is applied.

An endoscope system 14 shown in FIG. 1 includes a lighting apparatus 10 to which the present invention is applied, a video processor 11, an endoscope 12 and a TV monitor (indicator) 13. The lighting apparatus 10 can be connected to and disconnected from the video processor 11.

Figure 2:
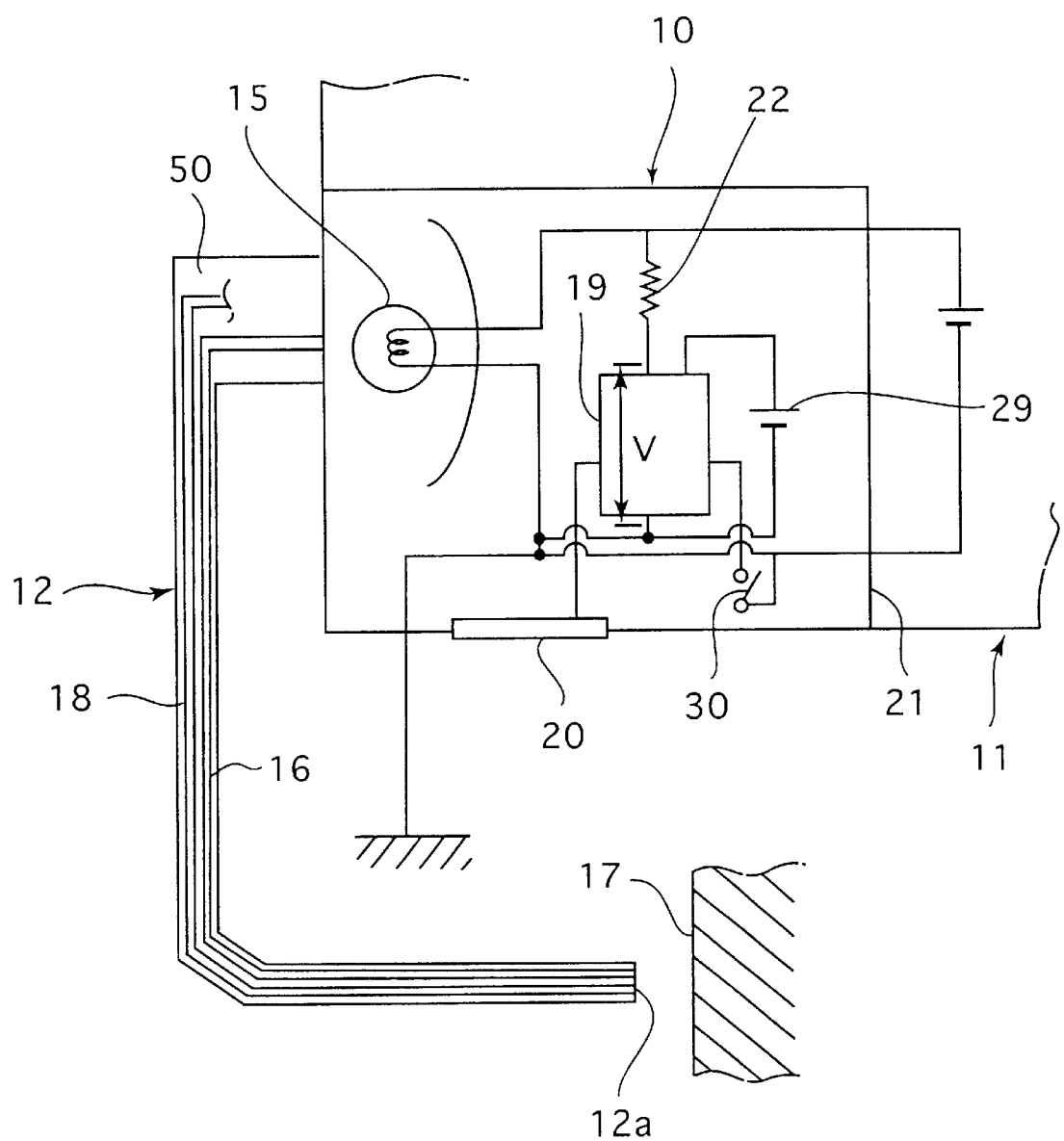
FIG. 2 is a schematic illustration showing the lighting apparatus shown in FIG. 1.

As shown in FIG. 2, the endoscope 12 is provided with a light guide 16 for leading the light emitted from a light source in the form of an electric bulb (e.g., a xenon arc lamp) 15 to an insertion tip (distal end) 12a of the endoscope 12, and an image guide 18 for transmitting the light reflected by a subject 17 to be examined (e.g., inner portion of a living body) to the video processor 11. The light guide 16 and the image guide 18 are each composed of an optical fiber. The video processor 11 is provided therein with an image pick-up device such as a CCD (not shown) and performs an image processing operation in which the aforementioned reflected light is converted into electrical image signals by the image pick-up device. The electrical image signals are output to the TV monitor 13 to be displayed thereon as an image of the subject 17. The endoscope 12 can be connected to and disconnected from the video processor 11 via a connector 50. Connecting the endoscope 12 to the video processor 11 allows each of the light guide 16 and the image guide 18 to be automatically connected to a corresponding connector (not shown) provided on the video processor 11.

The lighting apparatus 10 is provided as a unit including the bulb 15, a consumption (lighting time) recording circuit (recorder) 19 and an LCD (Liquid Crystal Display) panel 20 which are all accommodated in a casing 21. Power having a predetermined voltage is supplied to the bulb 15 from the video processor 11. The consumption recording circuit 19 is electrically connected in parallel with the bulb 15 via a resistor 22 so that the consumption recording circuit 19 can utilize the power supplied to the bulb 15 from the video processor 11. The resistor 22 functions to generate a predetermined recording voltage V between the terminals of the consumption recording circuit 19 by reducing the voltage of the supplied power.

Figure 3:
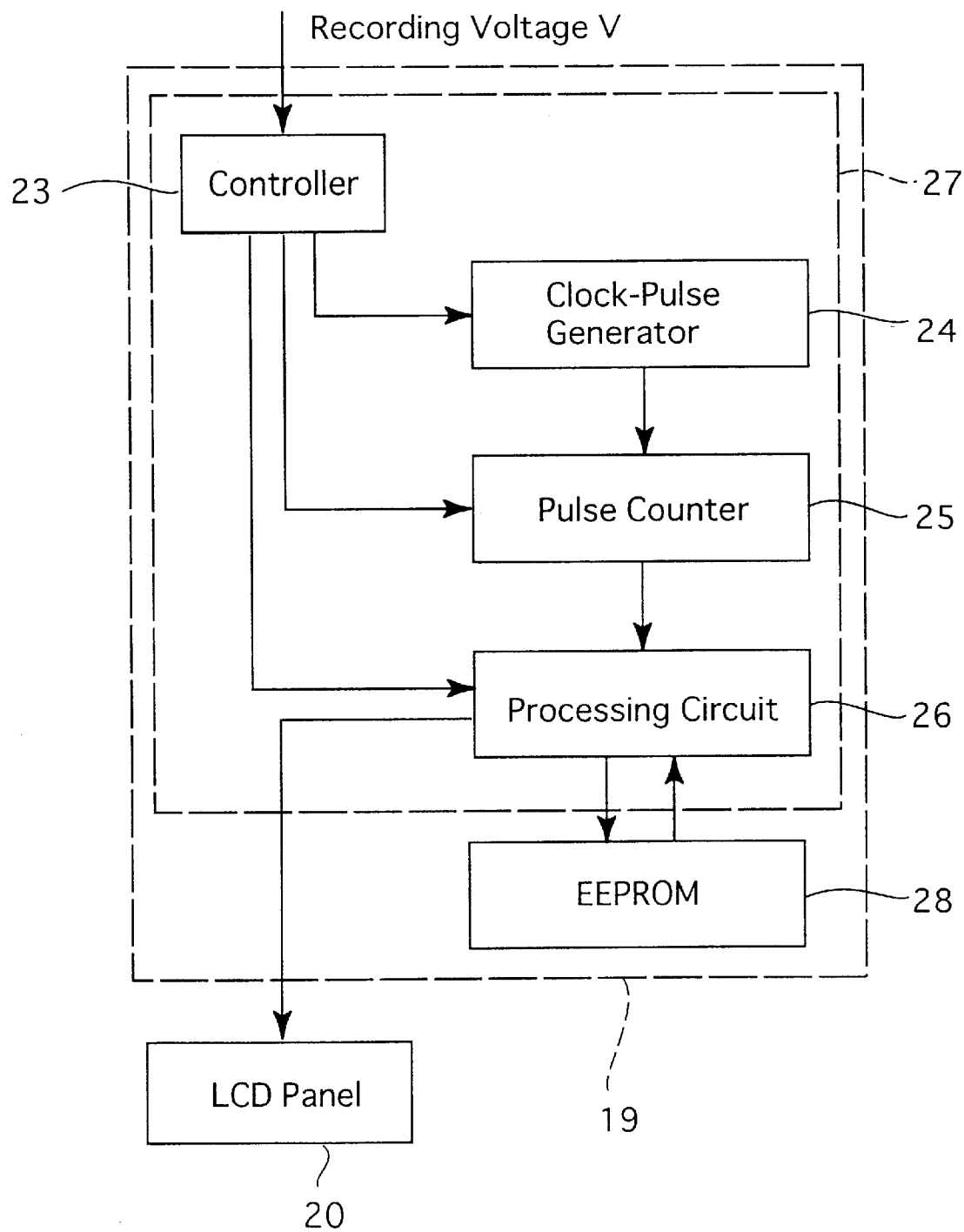
FIG. 3 is a block diagram showing the construction of a consumption recording device.
Figure 4:
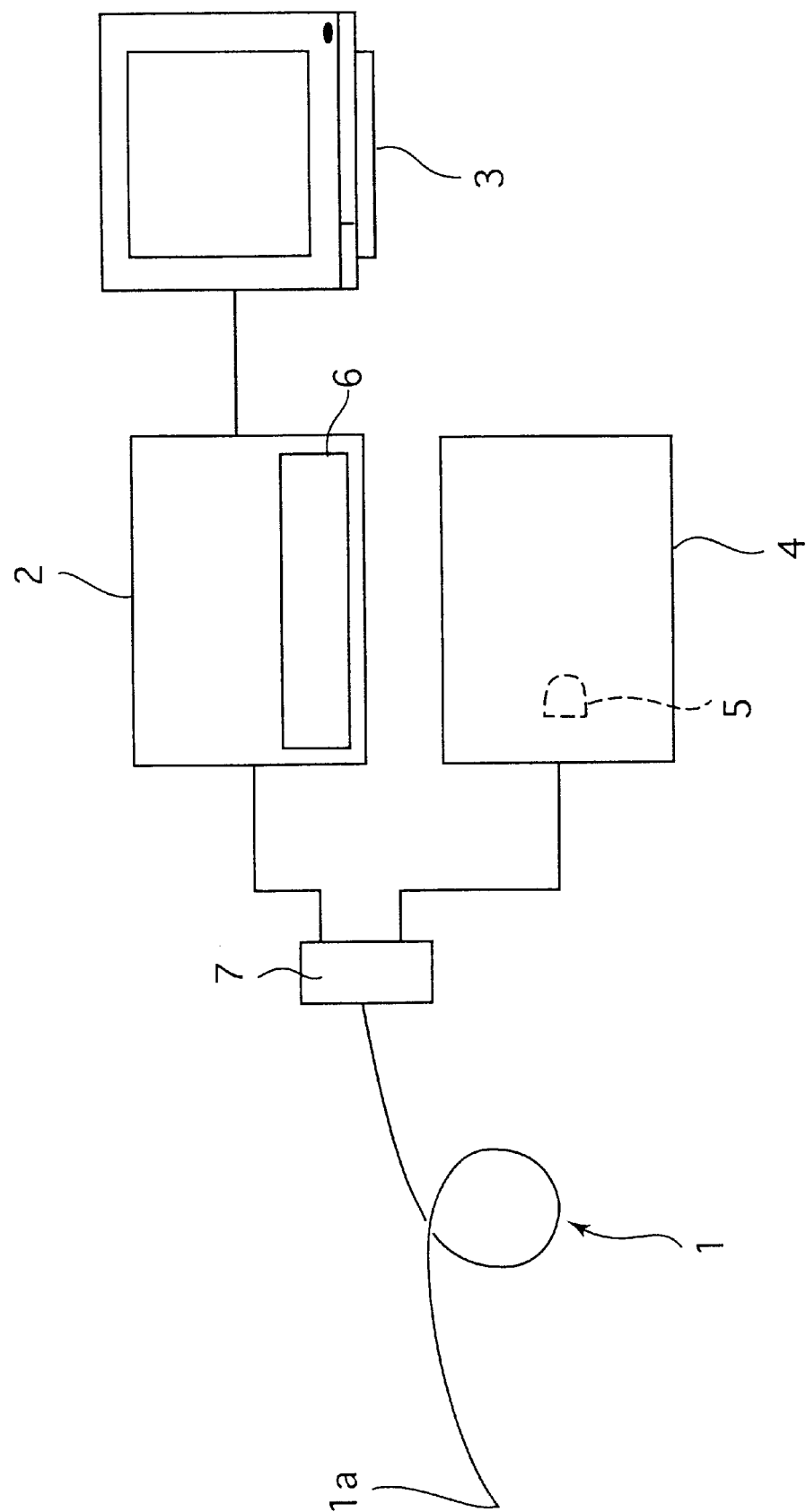
FIG. 4 is a schematic illustration showing a conventional endoscope system.

As shown in FIG. 3, the consumption recording circuit 19 includes a CPU 27 and an EEPROM 28. The CPU 27 includes a controller 23, a clock-pulse generator 24, a pulse counter 25 and a processing circuit 26. When power is supplied to the bulb 15, the recording voltage V is generated so that the controller 23 sends control signals only during the time of generation of the recording voltage V to control each of the clock-pulse generator 24, the pulse counter 25 and the processing circuit 26, in the following manner. Namely, the clock-pulse generator 24 is controlled to generate clock pulses in accordance with the period of generation of the recording voltage V, and the pulse counter 25 is controlled to count the number of the generated clock pulses. The processing circuit 26 accumulatively stores the number of the generated clock pulses in the EEPROM 28 as data of the total time of generation of the clock pulses; i.e., data (recording data) of the total consumed lighting-time of the bulb 15. The processing circuit 26 is further controlled to read out the recording data from the EEPROM 28 to visually indicate the information on the total consumed lighting-time of the bulb 15 (i.e., the total time of supplying power to the bulb 15) on the LCD panel 20.

The lighting apparatus 10 is provided with an auxiliary battery (backup battery) 29 for supplying power to the CPU 27 during the time the lighting apparatus 10 is disconnected from the video processor 11, i.e., during the time no power is supplied to the CPU 27 from the video processor 11. The lighting apparatus 10 is further provided with a reset switch 30 which initializes the EEPROM 28 to make the total consumed lighting-time of the bulb 15 zero (0) when the reset switch 30 is turned ON.

In the present embodiment of the lighting apparatus 10, the recording voltage V is applied to the bulb 15 only during the time the bulb 15 is ON (i.e., during the time of supplying power to the bulb 15), while the consumed lighting time (consumed light-emission time) of the bulb 15 is recorded by the consumption recording circuit 19 regardless of any other devices such as the video processor 11. Therefore, in accordance with the recorded data of the total consumed lighting-time of the bulb 15, the precise information about the life span of the bulb 15 such as the total consumed lighting-time of the bulb 15 and/or the remaining life of the bulb 15 can be indicated on the LCD panel 20. This makes it easy and accurate for the user to determine the time for the replacement of the bulb 15.

Since the lighting apparatus 10 is provided as a unit including the bulb 15, the consumption recording circuit 19, and the LCD panel 20 which are fundamental elements of the lighting apparatus 10; the bulb 15 can be promptly replaced by initially storing the value of the available bulb-life (remaining life) of the bulb 15 which is predicted in accordance with the life span of the bulb 15 (generally determined and made known to the user by the manufacturer of the bulb 15) in the EEPROM 28, and subsequently disconnecting the lighting apparatus 10 from the video processor 11 to replace the old lighting apparatus 10 with a new one when the user is informed that the total consumed lighting-time has reached the stored available bulb-life of the bulb 15 via the information indicated on the LCD panel 20. This prevents the amount of light emitted by the bulb 15 from decreasing due to usage over a long-term, and prevents the bulb 15 from burning out during the use of the endoscope system 14. The value of the available bulb-life of the bulb 15 which is predicted in accordance with the life span of the bulb 15 can be manually stored in the EEPROM 28 by the user of the endoscope system 14 by operating an input device (not shown). In the case where the bulb 15 is the only type available for the lighting apparatus 10, the value of the available bulb-life can be prestored as a fixed value in the EEPROM 28 or the like; namely, the value of the available bulb-life does not have to be manually stored in the EEPROM 28 by the user each time the bulb 15 is replaced by a new one. In the case where more than one type of bulb is available for the lighting apparatus 10, the value of the available bulb-life is manually stored in the EEPROM 28 or the like by the user each time the bulb is replaced by a new one.

The used lighting apparatus 10 disconnected from the video processor 11 can be reused by turning the reset switch 30 ON to initialize the EEPROM 28 after the bulb 15 is replaced by a new one. After the EEPROM 28 is initialized, the value of the available bulb-life which is predicted in accordance with the life span of a new bulb 15 can be newly stored in the EEPROM 28. The reset switch 30 can be replaced by a detector or sensor that automatically initializes the EEPROM 28 upon detecting that the lighting apparatus 10 is connected to, or disconnected from, the video processor 11.

Since power is supplied to each of the consumption recording circuit 19 and the bulb 15 from a common power source, it is unnecessary to provide the consumption recording circuit 19 with another power source to be exclusively used by the consumption recording circuit 19. This simplifies the structure of the endoscope system 14.

In the illustrated embodiment, although the EEPROM 28 is not part of the CPU 27, the EEPROM 28 can be incorporated in the CPU 27. Alternatively, the EEPROM 28 can be replaced by a RAM. In this case, power can be supplied to the RAM from the auxiliary battery 29 during the time the lighting apparatus 10 is disconnected from the video processor 11.

In the illustrated embodiment, although the endoscope system 14 is used with the lighting apparatus 10 being connected to the video processor 11, the endoscope system 14 can be modified to be used without the lighting apparatus 10 being connected to the video processor 11. Namely, the endoscope system 14 can be modified to be used with the lighting apparatus 10 being connected solely to the connector 50. In this case, power can be supplied to the lighting apparatus 10 from a battery accommodated in the lighting apparatus 10 or an external power source.

As can be understood from the foregoing, since the light emission time of the light source is directly recorded by the consumption recording device while the information on the remaining life of the light source is indicated by the indicating device, the time for replacing the bulb with a new one can be reliably and precisely determined to prevent the amount of light emitted by the bulb from decreasing due to usage over a long-term, and prevents the bulb from burning out during the use of the endoscope system.

Furthermore, since the consumption recording device operates by utilizing the power supplied to the light source, the structure of the endoscope system can be simplified.

Since the light source is replaceable, and the consumption recording device can be initialized by operating the reset switch; and accordingly, allowing the lighting apparatus to be recyclable.

Furthermore, the used lighting apparatus is replaced by a new light source every time the value of the total time of light emission of the light source reaches a predetermined value of the remaining life (bulb-life) of the light source which is initially determined in accordance with the usual life span of the light source. Accordingly, the amount of light emitted by the light source is prevented from decreasing due to usage over a long-term, and the light source is prevented from burning out while the endoscope system is in use.

Obvious changes may be made in the specific embodiments of the present invention described herein, such modifications being within the spirit and scope of the invention claimed. It is indicated that all matter contained herein is illustrative and does not limit the scope of the present invention.

What is claimed is:

1. A lighting apparatus for an endoscope, the lighting apparatus being provided with a video processor that supplies a power to the lighting apparatus, comprising:

a light source for emitting light which is transmitted to a distal end of the endoscope via a light guide of the endoscope;

a consumption recording device for recording the consumed light-emission time of said light source; and an indicating device for indicating information on the remaining life of said light source in accordance with data recorded in said consumption recording device;

wherein said light source, said consumption recording device and said indicating device are provided so as to be detachable from the video processor as a unit.

2. The lighting apparatus according to claim 1, wherein said consumption recording device operates when a recording voltage is applied to said light source to emit light therefrom.

3. The lighting apparatus according to claim 2, wherein said recording voltage is generated between terminals of the consumption recording device by a resistor reducing the voltage of power supplied to said light source.

4. The lighting apparatus according to claim 1, wherein light source is replaceable.

5. The lighting apparatus according to claim 1, further comprising a reset switch for initializing said consumption recording device to reset said recorded data.

6. The lighting apparatus according to claim 5, wherein said reset switch initializes said consumption recording device when said light source is disconnected from or connected to said living apparatus.

7. The lighting apparatus according to claim 1, wherein said light source is an electric bulb.

8. The lighting apparatus according to claim 1, further comprising a casing which accommodates said light source, said consumption recording device and said indicating device;

wherein said indicating device comprises an LCD fixed to said casing.

9. The lighting apparatus according to claim 1, further comprising an auxiliary battery comprising a part of the unit, the auxiliary battery supplying power to the consumption recording device while the unit is disconnected from the video processor and no power is supplied from the video processor.

10. A method of using an endoscopic system having an endoscope and said lighting apparatus according to claim 1, said method comprising replacing said light source with a new light source when said indicating device indicates information indicating that the value of the total time of light emission of said light source has reached a predetermined value.

11. A lighting unit provided on a video processor that supplies power to the lighting unit, comprising:

a replaceable electric bulb for emitting light which is transmitted to a distal end of an endoscope via a light guide of the endoscope;

a recorder which accumulatively stores the consumed lighting time of said electric bulb; and an indicator for indicating information on the remaining life of said electric bulb in accordance with data recorded in said recorder, wherein said lighting unit is detachable from the video processor.

12. The lighting unit according to claim 11, further comprising an auxiliary battery that supplies power to the consumption recording device while the lighting unit is disconnected from the video processor and no power is supplied from the video processor.

* * * * *